US005929036A

United States Patent [19]

McEver

[11] Patent Number: 5,929,036

[45] Date of Patent: *Jul. 27, 1999

[54] LIGAND OR GMP-140 SELECTIN AND METHODS OF USE THEREOF

[75] Inventor: Rodger P. McEver, Oklahoma City, Okla.

[73] Assignee: The Board of Regents of the University of Oklahoma, Norman, Okla.

[ * ] Notice: This patent is subject to a terminal disclaimer.

[21] Appl. No.: 08/469,543

[22] Filed: Jun. 6, 1995

Related U.S. Application Data

[62] Division of application No. 08/278,554, Jul. 21, 1994, which is a continuation of application No. 07/650,484, Feb. 5, 1991, abandoned, which is a continuation-in-part of application No. 07/554,199, Jul. 17, 1990, abandoned, which is a continuation-in-part of application No. 07/320,408, Mar. 8, 1989, Pat. No. 5,378,464.

[51] Int. Cl.[6] .......... C07K 1/00

[52] U.S. Cl. .......... 514/25; 514/21; 514/23; 530/395; 530/396; 530/402; 530/403

[58] Field of Search .......... 530/395, 396, 530/402, 403; 514/21, 23, 25

[56] References Cited

PUBLICATIONS

Fukuda et al., "Structures of Sialylated Fucosyl Polylactosaminoglycans Isolated from CML Cells" J. Biol. Chem., v. 260, n. 24, pp. 12957–12967, (1985).

Moore et al., "Identification of Specific Glycoprotein Ligand for P–Selectin CD62 on Myeloid Cells", (1992) Biosis Abs #92:429190.

Gahmberg et al., "Major O–Glycosylated Sialoglycoproteins . . . " J. Cell. Biochem., (May 1988) 37 (1), 91–105.

Carlsson et al. "Structural Variations O–Linked Oligosaccharides . . . " J. Biol. Chem. (1986), 261(27), 12787–95.

Carlsson et al., "Isolation & Characterization Leukosialin . . . " J. Biol. Chem., (1986), 261(27), 12779–86.

*Primary Examiner*—Cecilia J. Tsang
*Assistant Examiner*—Patrick R. Delaney
*Attorney, Agent, or Firm*—Dunlap, Codding & Rogers, P.C.

[57] ABSTRACT

Fucosylated sialyated lactosaminoglycan structures that bind to GMP-140 have been discovered. The structure is created by expression of α(1,3) fucosyltransferases capable of modifying acceptors containing α(2,3) sialic acid-substituted lactosaminoglycans. $Le^x$, Galβ1,4(Fucα1,3) GlcNAcβ1-R (where R is a protein or other carbohydrate structure), a common trisaccharide structure on myeloid cells but not on lymphocytes or erythroid cells, forms the core of this sialyated structure. The actual structure may be sialyl $Le^x$, difucosyl sialyl $Le^x$, a longer polyfucosylated polyactosaminoglycan, or a related variant. Several of these structures may bind to GMP-140 with various degrees of affinity. The carbohydrate structures, including sialyl $Le^x$, difucosyl sialyl $Le^x$, or a longer polyfucosylated polyactosaminoglycan variant, produced synthetically or expressed in genetically engineered cells, are useful as diagnostics and, in combination with a suitable pharmaceutical carrier, for clinical applications in the modulation or inhibition of coagulation processes or inflammatory processes. Antibodies to these structures can also be used as diagnostics and as pharmaceuticals for modulation of the coagulation or inflammatory processes.

18 Claims, 4 Drawing Sheets

LIGAND OR GMP-140 SELECTIN AND METHODS OF USE THEREOF

This is a divisional of prior application U.S. Ser. No. 08/278,554 filed on Jul. 21, 1994, by Rodger P. McEver entitled "Ligand for GMP-140 Selectin and Methods of Use Thereof, " which is a continuation of U.S. Ser. No. 07/650,484 filed Feb. 5, 1991, now abandoned, which is a continuation-in-part of U.S. Ser. No. 07/554,199 now abandoned filed Jul. 17, 1990 entitled "Functionally Active Selectin-derived Peptides", which is a continuation-in-part of U.S. Ser. No. 07/320,408 entitled "Method for Modulation of Inflammatory Responses" filed Mar. 8, 1989, now U.S. Pat. No. 5,378,464, by Rodger P. McEver.

The U.S. Government has rights in this invention by virtue of grants from the National Heart, Lung and Blood Institute.

BACKGROUND OF THE INVENTION

This invention is generally in the field of methods for the treatment and prevention of inflammatory responses involving binding reactions with the selectin GMP-140.

As described in U.S. Ser. Nos. 07/554,199 and 07/320,408, the teachings of which are incorporated herein, the adherence of platelets and leukocytes to vascular surfaces is a critical component of the inflammatory response, and is part of a complex series of reactions involving the simultaneous and interrelated activation of the complement, coagulation, and immune systems.

Endothelium exposed to "rapid" activators such as thrombin and histamine becomes adhesive for neutrophils within two to ten minutes, while endothelium exposed to cytokines such as tumor necrosis factor and interleukin-1 becomes adhesive after one to six hours. The rapid endothelial-dependent leukocyte adhesion has been associated with expression of the lipid mediator platelet activating factor (PAF) on the cell surface, and presumably, the appearance of other endothelial and leukocyte surface receptors. The slower cytokine-inducible endothelial adhesion for leukocytes is mediated, at least in part, by an endothelial cell receptor, ELAM-1, that is synthesized by endothelial cells after exposure to cytokines and then transported to the cell surface, where it binds neutrophils. The isolation, characterization and cloning of ELAM-1 is reviewed by Bevilacqua, et al., in *Science* 243, 1160–1165 (1989). A peripheral lymph node homing receptor, also called "the murine Mel 14 antigen", "Leu 8", the "Leu 8 antigen" and "LAM-1", is another structure on neutrophils, monocytes, and lymphocytes that binds lymphocytes to high endothelial venules in peripheral lymph nodes. The characterization and cloning of this protein is reviewed by Lasky, et al., *Cell* 56, 1045–1055 (1989) (mouse) and Tedder, et al., *J. Exp. Med.* 170, 123–133 (1989).

GMP-140 (granule membrane protein 140), also known as PADGEM, is a cysteine-rich and heavily glycosylated integral membrane glycoprotein with an apparent molecular weight of 140,000 as assessed by sodium dodecyl sulfate polyacrylamide gel electrophoresis (SDS-PAGE). GMP-140 was first purified from human platelets by McEver and Martin, *J. Biol. Chem.* 259: 9799–9804 (1984). The protein is present in alpha granules of resting platelets but is rapidly redistributed to the plasma membrane following platelet activation, as reported by Stenberg, et al., (1985). The presence of GMP-140 in endothelial cells and its biosynthesis by these cells was reported by McEver, et al., *Blood* 70(5) Suppl. 1: 355a, Abstract No. 1274 (1987). In endothelial cells, GMP-140 is found in storage granules known as the Weibel-Palade bodies. GMP-140 (called PADGEM) has also been reported to mediate the interaction of activated platelets with neutrophils and monocytes by Larsen, et al., in *Cell* 59, 305–312 (October 1989) and Hamburger and McEver, *Blood* 75: 550–554 (1990).

The cDNA-derived amino acid sequence, reported by Johnston, et al., in *Cell* 56, 1033–1044 (Mar. 24, 1989), and in U.S. Ser. No. 07/320,408 filed Mar. 8, 1989, indicates that it contains a number of modular domains that are likely to fold independently. Beginning at the N-terminus, these include a "lectin" domain, an "EGF" domain, nine tandem consensus repeats similar to those in complement binding proteins, a transmembrane domain (except in a soluble form that appears to result from differential splicing), and a cytoplasmic tail.

When platelets or endothelial cells are activated by mediators such as thrombin, the membranes of the storage granules fuse with the plasma membrane, the soluble contents of the granules are released to the external environment, and membrane bound GMP-140 is presented within seconds on the cell surface. The rapid redistribution of GMP-140 to the surface of platelets and endothelial cells as a result of activation suggests that this glycoprotein could play an important role at sites of inflammation or vascular disruption.

ELAM-1, the homing receptor, and GMP-140 have been termed "selecting", based on their related structure and function.

The in vivo significance of platelet-leukocyte interactions has not been studied carefully. However, in response to vascular injury, platelets are known to adhere to subendothelial surfaces, become activated, and support coagulation. Platelets and other cells may also play an important role in the recruitment of leukocytes into the wound in order to contain microbial invasion. Conversely, leukocytes may recruit platelets into tissues at sites of inflammation, as reported by Issekutz, et al., *Lab. Invest.* 49: 716 (1983).

The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Proteins involved in the hemostatic and inflammatory pathways are of interest for diagnostic purposes and treatment of human disorders. However, there are many problems using proteins therapeutically. Proteins are usually expensive to produce in quantities sufficient for administration to a patient. Moreover, there can be a reaction against the protein after it has been administered more than once to the patient. When, as appears to be the case for both ELAM-1 and GMP-140, as first described in U.S. Ser. No. 07/320,408, the receptor bound by the protein is a glycoprotein and the carbohydrate portion of the receptor plays a major role in the binding process, it is desirable to develop carbohydrate molecules which can be used both in vitro and in vivo to modulate binding by the selecting, as effectively as the protein molecules, but which are less expensive to synthesize, more reproducible and presumably potentially less likely to cause a reaction. In U.S. Ser. No. 07/320,408, it was proposed that inflammatory responses could be modified by employing sugars or oligosaccharides in the ligand or counterreceptor for GMP-140 on leukocytes. This was based on the presence of an N-terminal domain homologous to $Ca^{2+}$-lectins in GMP-140 and a similar domain in the lymphocyte homing receptor, for which there was evidence supporting a lectin-like interaction with target cells in which sialic acid might play an important role.

U.S. Ser. No. 07/554,199 disclosed that the ligand for GMP-140 contained critical sialic acid residues. This was based on reduction of binding of [$^{125}$I]GMP-140 to neutrophils pretreated with neuraminidase from *Vibrio cholera.* This neuraminidase cleaves sialic acid at both α2,3 and α2,6 linkages. It was proposed that the oligosaccharide structure might include the entity, sialyl $Le^x$, which is NeuAcα2, 3Galβ1,4(Fucα1,3)GlcNAcβ1-R. This was based on the fact that the $Le^x$ structure, Galβ1,4(Fucα1,3)GlcNAcβ1-R, is a common oligosaccharide structure on myeloid cells but not on lymphocytes or erythroid cells. The trisaccharide $Le^x$ is often found in repeating units, or polylactosamine chains, which are extended oligosaccharide structures on myeloid glycoproteins or glycolipids. The neuraminidase data indicated that $Le^x$ per se could not be the ligand, but it was possible that the ligand could be sialyl $Le^x$, or a longer sialylated, polyfucosylated polylactosaminoglycan of which sialyl $Le^x$ might be a part.

In November 1990, Larsen, et al, in *Cell* 63: 467–474 (1990), claimed that $Le^x$ is, or is a major "component" of the ligand, based on inhibition of neutrophil or HL60 cell binding to activated platelets (which express GMP-140) or to COS cells transfected with GMP-140 cDNA. The inhibition was either with high concentrations of monoclonal antibodies to $Le^x$ or with concentrations of LNFIII up to 300 μM. LNFIII is Galβ1,4(Fucα1,3)GlcNAcβ1,3Galβ1,4Glc; thus it includes the $Le^x$ trisaccharide.

Corral, et al., in *Biochem. Biophys. Res. Comm.* 172(3), 1349–1356 (November 1990), also stated that sialic acid residues are a key feature of the carbohydrate ligand for GMP-140. Their assay was the rosetting of activated platelets to neutrophils or HL60 cells. They could inhibit rosetting by pretreating neutrophils with neuraminidase from *Vibrio cholera,* in agreement with the findings disclosed in U.S. Ser. No. 07/554,199. However, they did not prevent rosetting with neuraminidase from Newcastle disease virus. Thus they inferred that the linkage is likely to be α2,6. However, since the Newcastle enzyme is part of an intact virus it is probable that the virus directly agglutinated platelets to neutrophils, obscuring the inhibitory effect of the neuraminidase.

At least four papers have appeared on the carbohydrate ligand for the related selectin, ELAM-1: Phillips, et al., *Science* 250: 1130–1131 (November 1990); Walz, et al., *Science* 250: 1132–1135 (November 1990); Lowe, et al., *Cell* 63: 475–484 (November 1990); and Goelz, et al., *Cell* 63: 1349–1356 (December 1990). These reports conclude that the ELAM-1 ligand is either sialyl $Le^x$ or a related sialylated fucosylated structure. All of the reports describing the ligand for ELAM-1 agree that it is a sialylated fucosylated structure, with at least some of the reports suggesting that the ligand is sialyl $Le^x$ per se.

Brandley, et al., in *Cell* 63: 861–863 (November 1990) review what is known about the ligands for the various selecting and the potential applications for these structures.

It is therefore an object of the present invention to provide the carbohydrate structures forming a part of the ligand or counterreceptor for the selectin GMP-140, which is distinct from the other selectins such as ELAM-1.

It is another object of the present invention to provide methods for using these carbohydrate structures to inhibit leukocyte adhesion to endothelium or to platelets.

It is a further object of the present invention to provide methods for using these carbohydrate structures to modulate the immune response and the hemostatic pathway.

SUMMARY OF THE INVENTION

Fucosylated sialyated lactosamine structures that bind to GMP-140 have been discovered. The structure is created by expression of α(1,3) fucosyltransferases capable of modifying acceptors containing α(2,3)sialic acid-substituted lactosaminoglycans. $Le^x$, Galβ1,4(Fucα1,3) GlcNAcβ1-R (where R is a protein or other carbohydrate structure), a common trisaccharide structure on myeloid cells but not on lymphocytes or erythroid cells, forms the core of this sialyated structure. The actual structure may be sialyl $Le^x$, difucosyl sialyl $Le^x$, a longer polyfucosylated polyactosaminoglycan, or a related variant. Several of these structures may bind to GMP-140 with various degrees of affinity.

Examples using Chinese Hamster Ovary (CHO) cell lines transfected with specific glycosyl transferases confirm that the oligosaccharide ligand for GMP-140 is a sialylated fucosylated structure, that the sialic acid linkage must be α2,3 to Gal and that the fucose linkage must be α1,3 to a GlcNac to which a Gal has been attached by a β1,4 linkage.

The carbohydrate structures, including sialyl $Le^x$, difucosyl sialyl $Le^x$, or a longer polyfucosylated polyactosaminoglycan variant, produced synthetically or expressed in genetically engineered cells, are useful as diagnostics and, in combination with a suitable pharmaceutical carrier, for clinical applications in the modulation or inhibition of coagulation processes or inflammatory processes. Antibodies to these structures can also be used as diagnostics and as pharmaceuticals for modulation of the coagulation or inflammatory processes.

BRIEF DESCRIPTION OF THE DRAWINGS

FIG. 1A, CHO binding to GMP-140, CHO+$Ca^{2+}$(—squares—), CHO−$Ca^{2+}$(—dark diamonds—); 1B, Lec 8 CHO binding to GMP-140, Lec 8+$Ca^{2+}$(—squares—), Lec 8−$Ca^{2+}$(—dark diamonds—); 1C, Neo Lewis CHO binding to GMP-140, Neo Lewis+$Ca^{2+}$) (—squares—), Neo Lewis, Neuraminidase (—dark diamonds—), and Neo Lewis, EDTA (—dark squares—); and 1D, HL60 cell binding to GMP-140, HL60+$Ca^{2+}$(—squares—), HL60, Neuraminidase (—dark diamonds—), and HL60, EDTA (—dark squares—).

DETAILED DESCRIPTION OF THE INVENTION

Figure 1A:
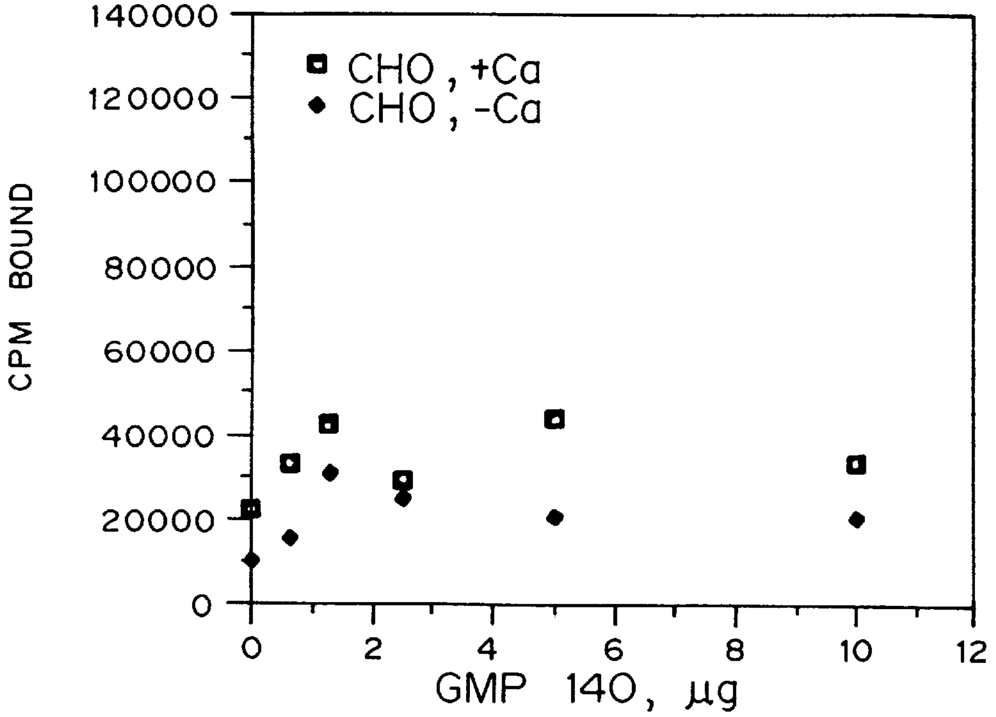
FIGS. 1A–1D are graphs of the binding of GMP-140 to HL-60 cells or to wild-type and transfected CHO cells, measured as CPM $^{51}$Cr, as a function of GMP-140 concentration used to coated the wells (μg GMP-140/ml), the presence or absence of $Ca^{2+}$, and neuraminidase treatment.

Fucosylated sialyated lactosamine structures that bind to GMP-140 have been discovered. The structure is created by expression of α(1,3) fucosyltransferases capable of modifying acceptors containing α(2,3)sialic acid-substituted lactosaminoglycans. $Le^x$, Galβ1,4(Fucα1,3) GlcNAcβ1-R (where R is a protein or other carbohydrate structure), a common trisaccharide structure on myeloid cells but not on lymphocytes or erythroid cells, forms the core of this sialyated structure. The actual structure may be sialyl $Le^x$, which is NeuAcα2-3Galβ1-4(Fucα1,3)GlcNAc-R. Other possible structures include difucosyl sialyl $Le^x$, a longer polyfucosylated polyactosaminoglycan, or a related variant. Several of these structures may bind to GMP-140 with various degrees of affinity.

The carbohydrate portion of the ligand is thought to be carried on one or more proteins on myeloid or other cells that interact with GMP-140. The myeloid glycoprotein(s) has not been isolated, but preliminary information about some of its features has been obtained.

This structure was deduced based on studies using protease and neuraminidase digestion, as well as transfected CHO cells.

As described in example 1, since binding is at least partially reduced by treating neutrophils with neuraminidase from the Newcastle disease virus, which cleaves sialic acid at α2,3 but not α2,6 linkages, as well as the neuraminidase from *Vibrio cholera,* at least some of the critical linkages in the ligand contain α2,3 linkages. Both types of enzymes also cleave α2,8 linkages, but these are not present on myeloid cells.

Other data with transfected cell lines described in detail in example 2 indicate that a sialyated fucosylated lactosamine with α2,3-linked sialic acid is sufficient for recognition. It is believed the carbohydrate is not $Le^x$ alone since an antibody to $Le^x$ does not block binding of [$^{125}$I]GMP-140 to neutrophils. Studies comparing binding of GMP-140 with two different multivalent neoglycoconjugates, in which either sialyl $Le^x$ or $Le^x$ was coupled to bovine serum albumin at a molar ratio of about 10:1, in high concentrations (6.5 μM of conjugate, 65 μM of oligosaccharide) also failed to inhibit binding, suggesting that neither $Le^x$ nor sialyl $Le^x$ per se is the ligand or that the affinity of these oligosaccharides for GMP-140 is too low to measure by this assay.

Evidence indicates that, while the carbohydrate portion of the glycoprotein ligand for GMP-140 is structurally similar to the carbohydrate portion of the glycoprotein ligand for ELAM-1, other studies indicate that differences exist in the recognition specificities of GMP-140 and ELAM-1. These may be due to slight differences in oligosaccharide structures recognized by each selectin or to different affinities of binding to the same structure.

It is possible that other oligosaccharide structures not described here may also interact with GMP-140. For example, a sialylated fucosylated lactosaminoglycan with an α2,6 sialic-acid linkage might bind; however, this structure has not been described in eukaryotic cells.

It is possible to manipulate binding of the GMP-140 to the ligand in vivo using the sialylated fucosylated lactosamine or a carbohydrate or protein molecule to which multiple sialyated fucosylated lactosamines have been attached. Using multiple sialylated fucosylated lactosamines attached to a single molecule may increase the affinity of the GMP-140 for the artificial molecule over the natural ligand.

EXAMPLE 1

Characterization of the "Ligand" or "Counter-receptor" for GMP-140 by Enzyme Digestion As described in U.S. Ser. No. 07/554,199, the ability of the lectin 19-34 peptide to prevent binding to GMP-140 of all three monoclonal antibodies that block interactions of GMP-140 with leukocytes provides additional proof of the importance of the lectin domain in leukocyte recognition. It is postulated from this data that the conformation of the lectin domain is modulated by interactions with the EGF domain; these interactions in turn are modulated by divalent cations, which may bind to both the lectin and EGF domains. The result is a three-dimensional conformation of the lectin domain that confers affinity and specificity of binding to its receptor(s) on neutrophils and monocytes.

Neutrophils were isolated, suspended to $4\times10^6$/ml in $Ca^{2+}/Mg^{2+}$-free HBSS, supplemented with 1 mg/ml HSA and 1 mM $Ca^{2+}$(HBSS/HSA/Ca), and kept at 4° C. until used.

Neutrophils were treated with proteases, either trypsin or elastase, to determine if the receptor contains a protease-sensitive protein component. Neutrophils, suspended in HBSS/10 mM MOPS, pH 7.5 (HBSS/MOPS), were treated twice at 22° C. for 10 min with 2 mM diisopropylfluorophosphate (DFP) to inactivate endogenous serine proteases. The cells were then washed with HBSS/MOPS and fixed with one-eight volume of 8% paraformaldehyde for 30 min at 22° C., followed by addition of one-eighth volume of 0.5 M glycine/0.25 M Tris, pH 7.5. Fixed neutrophils ($7.5\times10^6$/ml) in HBSS/MOPS, were incubated at 37° C. with TPCK-trypsin (0.77 μM, 41 U/ml) for 10 min or with elastase (40 μM, 7.8 U/ml) for 30 min. Control cells were incubated under identical conditions with the same concentrtions of enzyme previously inactivated with DFP or buffer alone. After the incubation period, DFP was added to 2 mM and the cells were pelleted at 400 g for 5 min. The cells were resuspended with HBSS/MOPS and DFP was added again to 2 mM. After centrifugation at 400 g for 5 min, the cell pellets were resuspended to $4\times10^6$/ml in HBSS/human serum albumin (HSA)/Ca and specific binding of [$^{125}$I]GMP-140 was determined. DFP-treated fixed neturophils ($1.6\times10^7$/ml) in 0.15 M NaCl, 50 mM acetate, pH 6.0, 10 mg/ml HSA, 9 mM $CaCl_2$, 0.05% sodium azide (digestion buffer) were incubated with neuraminidase, endo-β-galactosidase, or buffer for varying time periods at 37° C. in the presence of 20 μM leupeptin, 30 μM antipain, 0.64 mM benzamidine, and 100 KIU/ml aprotinin. In some incubations, 0.5 to 20 mM of the neuraminidase inhibitor Neu2en5Ac, dissolved in digestion buffer, was included. At these concentrations the pH of the reaction mixture was not affected by the inhibitor. After enzyme treatment, the cells were washed twice with cold HBSS/HSA/Ca and resuspended in HBSS/HSA/Ca to $4\times10^6$/ml before measurement of [$^{125}$I]GMP-140 binding. The NDV neuraminidase used was a suspension of virus particles, each of which contains approximately $10^3$ neuraminidase molecules, whereas the *V. cholerae* enzyme is in solution.

Binding of [$^{125}$I]GMP-140 to neutrophils was decreased to 4 to 5% by the proteases, but not by elastase or trypsin inactivated with diisopropylfluorophosphate, indicating that at least a substantial fraction of the leukocyte counter-receptors for GMP-140 contain, or are associated with, a protease-sensitive protein component.

Neutrophils were treated with neuraminidase from either *Vibrio cholera* (Boehringer-Mannheim Biochemicals, Indianapolis, Ind.) or Newcastle disease virus (NDV) (isolated as described by Paulson, J. C., et al., *J. Biol. Chem.* 254: 2120–2124 (1979)) and endo-β-galactosidase from *Bacteroides fragilis* (Boehringer-Mannheim). Neuraminidase from *V. cholera* cleaves α2-3-, α2-6-, and α2-8-linked sialic acids. NDV neuraminidase cleaves only α2-3- and α2-8-linked sialic acids.

Treatment of neutrophils with neuraminidase purified from *Vibrio cholera* greatly decreased both binding of $^{125}$[GMP-140] to human neutrophils and adhesion of neutrophils to immobilized GMP-140, indicating that sialic acid residues constitute an essential component of the leukocyte counter-receptor(s) for GMP-140. After 10 to 30 min of incubation with 0.1 to 0.2 U/ml of *V. cholera* or NDV neuraminidase, specific GMP-140 binding decreased to 28±9 and 52±9% (mean±SD, n=7), respectively, when compared with sham-treated controls. To minimize the possibility that this effect was due to either endogenous neutrophil proteases or protease contamination in the neuraminidase preparations, neutrophils were treated with DFP before fixation to inactivate endogenous serine proteases, and the neuraminidase incubations were performed in the presence of 10 mg/ml HSA as well as several protease inhibitors. The specificity of the neuraminidase effect was further demonstrated by the ability of a competitive neuraminidase inhibitor, Neu2en5Ac, to prevent the neuraminidase-induced reduction in GMP-140 binding to neutrophils. Neu2en5Ac inhibited the effect of neuraminidase in a dose-dependent manner with an $IC_{50}$ of 2.5 mM.

These results indicate that the counter-receptor, or ligand, on leukocytes for GMP-140 is a glycoprotein wherein sialic acid is required for receptor function. Neutrophils contain both α2-3- and α2-6-linked sialic acids, but α2-8-linkages have not been detected. Partial loss of GMP-140 binding after treatment with NDV neuraminidase implies that at least some of the sialic acid linkages in the receptor are of the α2-3-type. The greater inhibition observed using the *V. cholera* enzyme may mean that α2-6-linkages are also required for receptor function, or the results may be due to lack of accessibility of all essential linkages by the NDV enzyme, which is part of an intact virus.

Myeloid cells, in contrast to erythroid cells and lymphoid cells, are rich in polylactosaminoglycans which can terminate in α2-3- or α2-6-linked sialic acids. Many of these lactosaminoglycans are fucosylated. These structures are present on both neutrophil glycoproteins and glycolipids. To examine the possible role of these glycans in GMP-140 recognition, cells were treated with endo-β-galactosidase, which hydrolyzes the β1-4 linkage between galactose and N-acetylglucosamine (Galβ1-4GlcNAc) in unbranched polylactosaminyl side chains of glycoproteins. Pretreatment of fixed neutrophils with up to 0.2 U/ml of *E. freundii* endo-β-galactosidase for 30 min, or up to 0.4 U/ml of *B. fragilis* endo-β-galactosidase for 60 min, had no effect on specific binding of GMP-140. The lack of effect of these enzymes on binding is consistent with the GMP-140 recognition structure not being on a polylactosmine side chain. Alternatively and perhaps more likely, the relevant side chains may not be susceptible to enzymatic hydrolysis under these conditions. Highly fucosylated and/or branched polylactosmainoglycans may be resistant to hydrolysis by this enzyme, although branched polylactosaminoglycans are not present in neutrophils. In addition, a single lactosaminoglycan linked directly to the core of an N- or O-linked structure would be resistant to the enzyme.

EXAMPLE 2

Demonstration of Requirements of Sialyated Fucosylated Structure for Binding of GMP-140

The following studies were done by Richard Cummings at the University of Georgia using Chinese Hamster Ovary cells, or CHO cells. The CHO cell lines that were used included Ade-C cells and Ade-C cells permanently transfected with specific glycosyl transferases. The Ade-C cells were selected because they contain very low levels of endogenous α(1,3)fucosyltransferases; these cells are denoted as wild type cells in the studies to be described. The transfected cells express certain types of oligosaccharides not present on the wild type cells. Another CHO cell line used, designated Lec8 CHO, is deficient in the transporter for UDPGal and the cells consequently lack galactosylated and sialylated glycoconjugates (Deutscher and Hirschberg, *J. Biol. Chem.* 261: 96–100, 1986). The oligosaccharide structures present on some of these cells and the cell types are shown in Table 1. The relevant cells are: wild type (CHO), Neo Lewis (Neo Lew), Neo Lewis related (Neo Lew (rel)), and Lec8 CHO (Lec8).

TABLE 1

OLIGOSACCHARIDE STRUCTURE OF CELL TYPES

| OLIGOSACCHARIDE STRUCTURES | | COMMON DESIGNATION | CELL TYPE |
|---|---|---|---|
| | Galβ1-4GlcNAcβ1-3Galβ1-4GlcNAcβ1-3Galβ1-4GlcNAcβ1 | i-Type 2 | CHO, NeoLewis, NeoLew(Rel), NeoH, Lec8 |
| NeuAcα2-3 | Galβ1-4GlcNAcβ1-3Galβ1-4GlcNAcβ1-3Galβ1-4GlcNAcβ1 | S2,3-i-Type 2 | CHO, NeoLewis, NeoLew(Rel), NeoH |
| NeuAcα2-6 | Galβ1-4GlcNAcβ1-3Galβ1-4GlcNAcβ1-3Galβ1-4GlcNAcβ1 | S2,6-i-Type 2 | |
| Galα1-3 | Galβ1-4GlcNAcβ1-3Galβ1-4GlcNAcβ1-3Galβ1-4GlcNAcβ1 | Galα1,3-i-Type 2 | |
| Fucα1-2 | Galβ1-4GlcNAcβ1-3Galβ1-4GlcNAcβ1-3Galβ1-4GlcNAcβ1 | Neo-H | NeoH |

TABLE 1-continued

OLIGOSACCHARIDE STRUCTURE OF CELL TYPES

| OLIGOSACCHARIDE STRUCTURES | COMMON DESIGNATION | CELL TYPE |
|---|---|---|
| Fucα1-3<br>\|<br>Galβ1-4GlcNAcβ1-3Galβ1–4GlcNAcβ1-3Galβ1-4GlcNAcβ1 | SSEA-1 | NeoLew,<br>NeoLew(Rel) |
| NeuAcα2-3　　Fucα1-3<br>　　　　　　　\|<br>　　　Galβ1-4GlcNAcβ1-3Galβ1–4GlcNAcβ1-3Galβ1-4GlcNAcβ1<br>α | S-Le$^x$ | NeoLew |
| NeuAcα2-3　　　　　　　　　　　Fucα1-3<br>　　　　　　　　　　　　　　　　\|<br>　　　Galβ1-4GlcNAcβ1-3Galβ1–4GlcNAcβ1-3Galβ1-4GlcNAcβ1<br>α | VIM-2 | NeoLew,<br>NeoLew(Rel) |
| NeuAcα2-3　　Fucα1-3　　　　Fucα1-3<br>　　　　　　　\|　　　　　　　\|<br>　　　Galβ1-4GlcNAcβ1-3Galβ1–4GlcNAcβ1-3Galβ1-4GlcNAcβ1<br>α | difucosyl-S-Le$^x$ | NeoLew |

The following methods were used to culture and transfect the cells:

The CHO line Ade-C (Oates and Patterson, *Som. Cell Genet.* 3: 561–577 (1977); Van Keuren et al., *Am. J. Hum. Genet.* 38: 793–804 (1986)) was grown in α-modified Eagle's medium supplemented with 10% fetal calf serum. Transfected CHO cells were grown in media supplemented with G418 (GIBCO) at 400 µg/ml (active drug).

The Neo Lewis CHO cells were prepared by stably transfecting Ade-C CHO cells with DNA encoding an α(1, 3/1,4)fucosyltransferase as previously described (Lowe et al., *Cell* 63: 475–484, 1990; the cells were referred to as CHO-FT in this reference). The Neo Lewis (rel) cells were prepared by stably transfecting wild type CHO cells with similar methods with DNA encoding an α(1,3) fucosyltransferase that catalyzes transfer of GDP fucose only to nonsialylated lactosaminoglycans; this transferase is described in Lowe et al., *Cell* 63: 475–484, 1990. Both of the transfected cell lines were gifts from Dr. John Lowe, University of Michigan.

Results and Conclusions

The structures produced by wild type CHO and transfected CHO cells are shown in Table 1. The wild type CHO cells express repeating Galβ1,4GlcNAcβ1,3 disaccharide units, some of which have a terminal sialic acid (NeuAc) linked α2,3. They do not have α2,6-linked sialic acid linkages and they do not have fucose linkages. In addition, they synthesize Type II structures (3Galβ1,4GlcNAcβ1) but not Type I structures (3Galβ1,3GlcNAcβ1). The NeoLewis cells have been transfected with a cDNA encoding an α1,3(4) fucosyltransferase, which uses GDP fucose as a donor and catalyzes addition of fucose to Galβ1,4GlcNAc-R to yield Galβ1,4(Fucα1,3)GlcNAc-R; this is the Le$^x$ structure (sometimes also known as the SSEA-1 antigen). The same enzyme transfers fucose to the sialylated substrate NeuAcα2,3Galβ,3 1,4GlcNAc-R to yield NeuAcα2, 3Galβ1,4(Fucα1,3)GlcNAc-R; this is the sialyl Le$^x$ structure. Two other related structures, VIM-2 and difucosyl Le$^x$, are also made by the NeoLewis cells, as shown in the table, as well as a variety of other sialylated polyfucosylated poly-N-acetyllactosamine-type structures. The NeoLewis related cells have been transfected with a different fucosyl transferase, an α1,3 fucosyltransferase which catalyzes transfer of GDP fucose only to nonsialylated substrates of Galβ1,4GlcNAc-R. This yields the Le$^x$ structure (see table).

To test the ability of these cells to interact with GMP-140, a slight modification of the adhesion assay used for neutrophils and HL60 cells (J.-G. Geng et al, *Nature* 343: 757–760, 1990) was used with purified GMP-140 and monoclonal antibodies to GMP-140. GMP-140 was immobilized on plastic wells in increasing concentrations and the wells were then blocked with albumin-containing buffer. CHO or HL-60 cells, metabolically labeled with [$^{35}$S]methionine, were added to the wells in the presence or absence of Ca$^{2+}$, and adhesion was measured by solubilizing the bound cells and quantitating the radioactivity.

The results of the binding assays are shown in FIGS. 1A (CHO binding to GMP-140); 1B (Lec 8 CHO binding to GMP-140); 1C (NeoLewis CHO binding to GMP-140); and 1D (HL60 cell binding to GMP-140).

Figure 2:
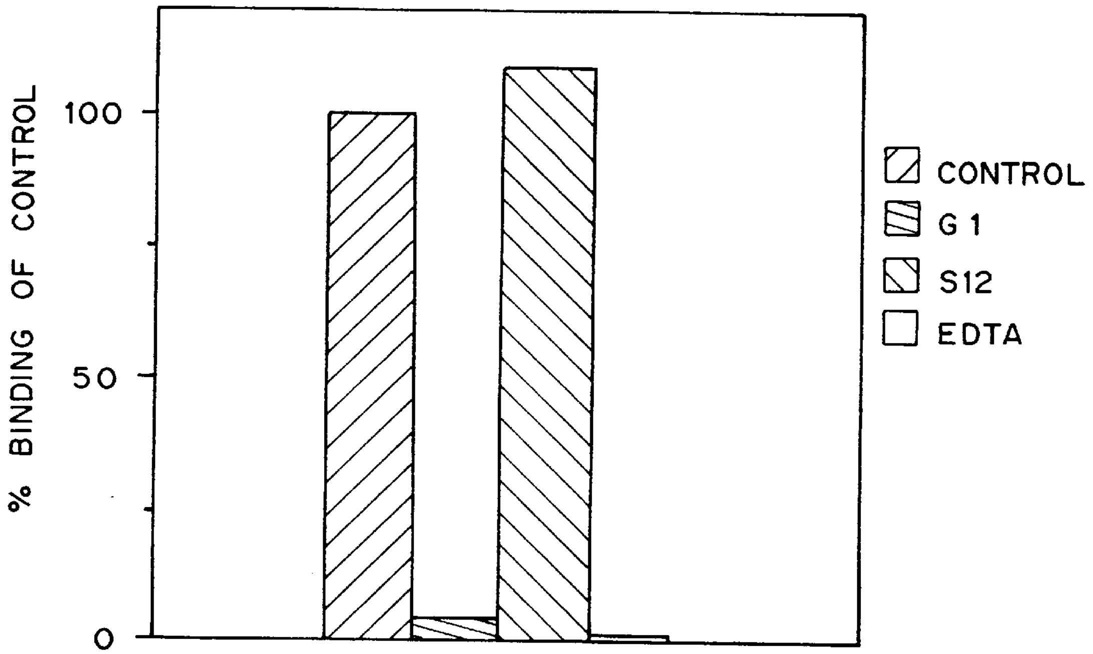
FIG. 2 is a graph of the effect of monoclonal antibodies on the binding of NeoLewis CHO cells to immobilized GMP-140, % binding of control for control (dark bar), in the presence of G1 antibody (///), in the presence of S12 antibody (++++), and in the presence of EDTA (/ / /).

The HL-60 cells bound specifically to GMP-140-coated wells in a Ca$^{2+}$-dependent manner, as previously noted (Geng, et al, *Nature* 343: 757–760 (1990)). The wild type CHO cells, the Lec 8 CHO cells, and the NeoLewis related CHO cells did not bind. However, like the HL-60 cells, the NeoLewis CHO cells bound avidly to immobilized GMP-140 in a Ca$^{2+}$-dependent manner. The adhesion was specific, because it was prevented by G1, a blocking monoclonal antibody to GMP-140, but not by S12, a nonblocking antibody, as shown in FIG. 2. The adhesion was critically dependent on sialic acid, because treatment of the NeoLewis CHO cells with neuraminidase from *Vibrio cholera* abolished binding. Pretreatment of the NeoLewis CHO cells with trypsin reduced binding by 60%, suggesting that at least a substantial fraction of the oligosaccharide ligands for GMP-140 on the cells are carried by a protein(s).

These data confirm that the oligosaccharide ligand for GMP-140 is a sialylated fucosylated structure. The sialic acid linkage must be α2,3 to Gal, because the CHO cells do not have α2,6 linkages. The fucose linkage must be α1,3 to a GlcNAc to which a Gal has been attached by a β1,4 linkage. Possible structures include sialyl Le$^x$ itself, difucosyl sialyl Le$^x$, a longer polyfucosylated polylactosaminoglycan variant of sialyl $Le^x$, or a branched structure containing elements of the above components. $Le^x$ itself does not provide the necessary affinity or specificity for binding. VIM-2, a sialylated structure lacking a Fuc linked to the GlcNAc closest to the terminal sialic acid, may not have affinity for GMP-140, since this structure is present on the NeoLewis related cells which do not bind to GMP-140. However, the quantities of VIM-2 on the Neo Lewis related cells are not known; if they are low, then the cells might not bind well even though there is some affinity of VIM-2 for GMP-140.

Although a recent study has indicated that high concentrations of $Le^x$ inhibit adhesion, LNFIII, which includes the $Le^x$ trisaccharide, in concentrations up to 300 μM has absolutely no effect on binding of neutrophils to purified, immobilized GMP-140.

EXAMPLE 3

Demonstration of Differences in Binding of Ligands by GMP-140 and ELAM-1

Despite data indicating that the ligands for ELAM-1 and GMP-140 are the same or very similar, there are two lines of evidence that the two molecules have different recognition specificities.

First, neutrophils adhere specifically to COS cells transfected with cDNAs encoding either GMP-140 or ELAM-1. As previously noted by Geng, et al, *Nature* (1990), adhesion to GMP-140-transfected cells was blocked by G1, a monoclonal antibody to GMP-140, and adhesion to ELAM-1-transfected cells was blocked by H18/7, a monoclonal antibody to ELAM-1. However, while fluid-phase GMP-140 blocked neutrophil adhesion to GMP-140-transfected cells, it had no effect on adhesion to ELAM-1-transfected cells (FIG. 3).

Figure 4:
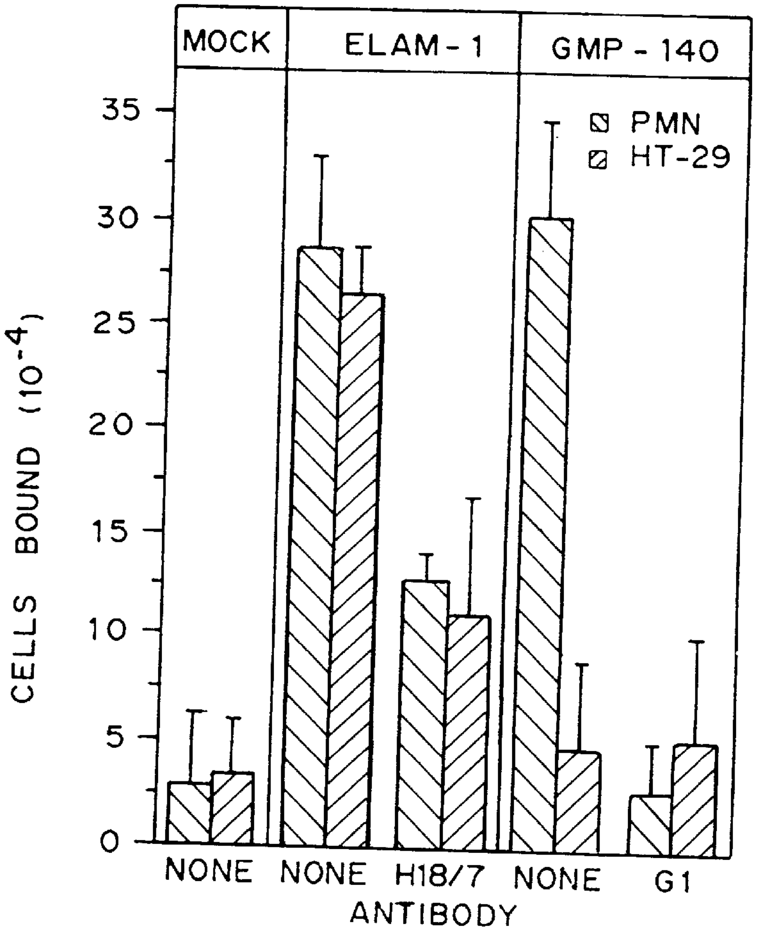
FIG. 4 is a graph of neutrophils (polymorphonuclear leukocytes or PMN) and HT-29 cells (which express sialyl $Le^x$) bound ($\times 10^{-4}$) by transfected COS cells: control, by ELAM-1 alone or in the presence of H18/7 antibody which blocks binding by ELAM-1 but not GMP-140, and by GMP-140 alone or in the presence of G1 antibody which blocks binding by GMP-140 but not ELAM-1.

Second, a human carcinoma cell line, HT-29, which contains abundant amounts of sialyl $Le^x$, binds to ELAM-1-transfected cells, but not to GMP-140-transfected cells (FIG. 4).

Figure 3:
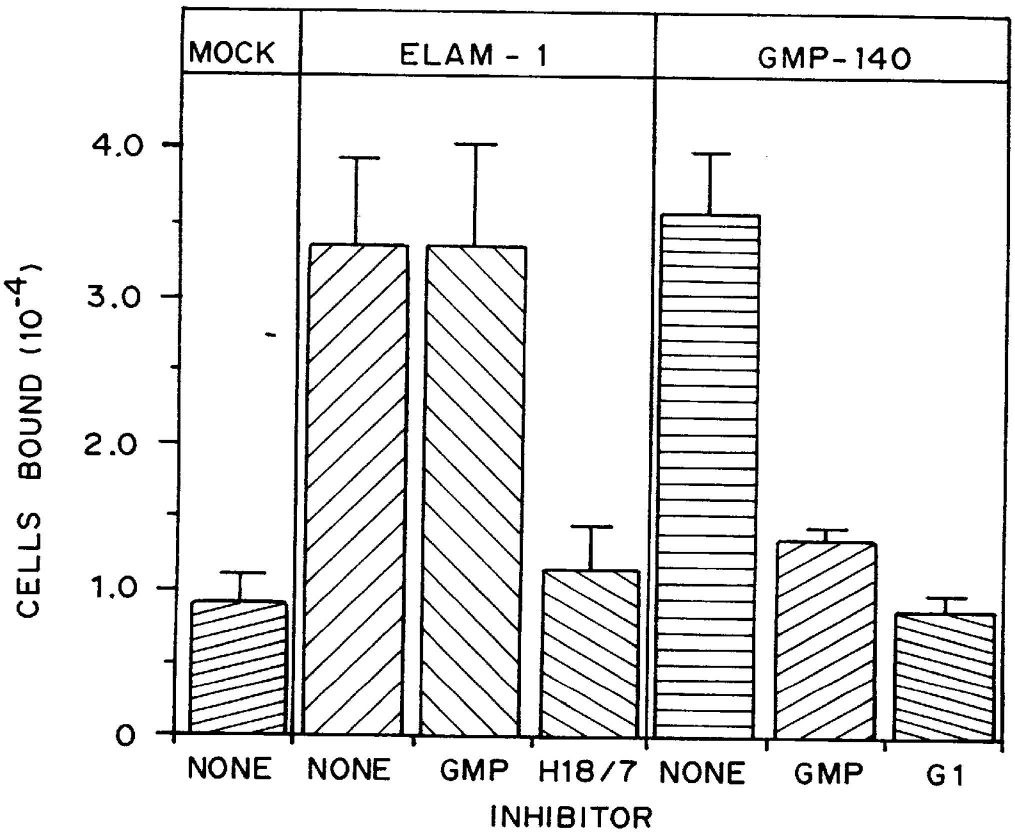
FIG. 3 is a graph of neutrophils bound (×$10^{-4}$) by monolayers of COS cells transfected with no cDNA (Mock) or with cDNAs encoding either ELAM-1 or GMP-140 in the presence or absence of fluid-phase inhibitors of binding. The inhibitors were: for ELAM-1-transfected cells—none, GMP-140, and H18/7 (a monoclonal antibody that recognizes ELAM-1 but not GMP-140 binding and blocks neutrophil adhesion to ELAM-1); and for GMP-140-transfected cells—none, GMP-140 (GMP), and G1 (a monoclonal antibody that recognizes GMP-140 but not ELAM-1 and blocks neutrophil adhesion to GMP-140).

The data in FIGS. 3 and 4 suggest that GMP-140 and ELAM-1 recognize ligands of somewhat different structure and/or that they differ in the affinity with which they recognize identical ligands. It is possible that GMP-140 and ELAM-1 each binds to a range of related oligosaccharide structures with different degrees of affinities.

The methods and materials used for the studies comparing binding by ELAM-1 and GMP-140 were as follows:

Cell Isolation and Culture

Human neutrophils were isolated from normal volunteers using Monopoly resolving media (Flow Labs) as described by Moore, et al., *J. Cell Biol.* 112, 491–499 (1991). Human HL-60 promyelocytic cells and HT-29 human colon carcinoma cells were obtained from the American Type Culture Collection (Rockville, Md.). HL-60 cells were maintained in RPMI-1640/10% fetal bovine serum. HT-29 cells were maintained in culture in McCoy's 5a medium supplemented with 10% fetal calf serum (fcs). COS-7 cells were maintained in Dulbecco's Modified Eagles Media (HG-DMEM) supplemented with 10% calf serum.

COS7 Cell Transfection and Neutrophil Rosetting Assay

Full-length cDNAs encoding GMP-140 or ELAM-1 were inserted into the CDM8 vector as previously described (Geng et al., *Nature,* 1990). COS7 cells were grown to approximately 80% confluency in 10 cm petri dishes in high glucose DMEM (Gibco) supplemented with 10% calf serum (HG-DMEM/10% CS). Fifty μl of Transfectin™ reagent (BRL Life Technologies, Inc.) was combined with 20 μg cDNA in 50 μl water or water alone and allowed to stand for 15 min at room temperature. After the COS cells were washed twice with 3 ml Opti-MEM™ I Reduced Serum Serum Media (BRL Life Technogies, Inc.), the cDNA-lipofectin reagent mixture was added and incubated overnight at 37° C. in a 5% $CO_2$ atmosphere. Six ml HG-DMEM/10% CS was added and the cells incubated for an additional 24 hours. The monolayers were then washed once with HBSS without $Ca^{+2}$ and $Mg^{+2}$, the cells detached with 0.02% EDTA, pelleted by centrifugation, then resuspended in 12 ml HG-DNEK/10% CS. Two ml of the cell suspension were plated into each well of a 6-well tissue culture (Corning) containing 3 ml HG-DMEM/10% CS and grown for an additional 24 hours. Prior to adhesion assays the wells were washed twice with HBSS. Duplicate wells were incubated with 0.5 ml HBSS containing 30 μg/ml of G1 $F(ab')_2$, or H18/7 $F(ab')_2$ or buffer alone for 30 min at 22° C. One ml freshly isolated human neutrophils ($2\times10^6$/ml in HBSS) that was incubated for 30 min in the presence of 30 μg/ml GMP-140 or diluent, were then added to the monolayers and incubated for 20 min at 22° C.

One ml of freshly isolated human neutrophils or $^{35}S$-methionine-labeled HT-29 cells ($2\times10^6$ in HBSS/1% HSA) was added and incubated for 20 min at 22° C. In some experiments neutrophils were incubated with purified GMP-140 (10 μg/ml final concentration) for 30 min at 22° C. prior to the adhesion assay.

To assay cell adhesion, after five washes with 5 ml HBSS/1% HSA, adherent neutrophils were solubilized with 200 μl 0.5% hexadecyltrimethyl ammonium bromide in 50 mM potassium phosphate pH 6.0. The number of adherent neutrophils was assayed in duplicate using a myeperoxidase assay as described by Geng, et al., Nature 343, 757–760 (1990). To assay HT-29 cell adhesion, adherent cells were solubilized with 1% Triton X100 and quantitated by liquid scintillation counting. Prior to addition of detergent, the monolayers were examined by phase contrast microscopy to confirm that they were adequately washed and that the COS cell monolayer remained intact.

Results

GMP-140 inhibits neutrophil adhesion to COS7 cells transfected with cDNA encoding GMP-140 but not to cells transfected with cDNA encoding ELAM-1. COS7 cells were either mock transfected or transfected with cDNAs encoding GMP-140 or ELAM-1. The ability of purified GMP-140, G1 $F(ab')_2$ or H18/7 $F(ab')_2$ (all at 10 μg/ml, final concentration) to inhibit neutrophil rosetting to transfected COS7 cells is shown in FIG. 3. The data represent the results from two independent transfection experiments. For each transfection, adhesion assays were performed on duplicate monolayers in the presence or absence of GMP-140 and either G1 $F(ab')_2$ or H18/7 $F(ab')_2$. Results are expressed as the number of neutrophils bound (mean±SD).

The results clearly demonstrate that neutrophils bind to COS cells transfected with cDNAs encoding either ELAM-1 or GMP-140 and that the binding is inhibited by appropriate monoclonal antibodies: the anti-ELAM-1 antibody (H18/7) blocks binding of neutrophils to ELAM-1-transfected cells and the anti-GMP-140 antibody (G1) blocks binding of neutrophils to GMP-140-transfected COS cells. However, fluid-phase GMP-140, while completely blocking neutrophil adhesion to GMP-140-transfected COS cells, has no effect on neutrophil adhesion to ELAM-1-transfected COS cells.

The transfected COS cells were then used to assess differences in binding of HT-29 cells, which contain large amounts of the sialyl $Le^x$ structure. The results, shown in FIG. 4, demonstrate that HT-29 cells bind avidly to ELAM-1-transfected cells but not at all to GMP-140-transfected cells. Therefore, interactions of HT-29 cells with GMP-140- and ELAM-1-transfected COS cells are not identical, even though GMP-140 and ELAM-1 both recognize oligosaccharide strutures containing α(2,3)sialylated, α(1,3)fucosylated lactosaminoglycans.

EXAMPLE 4

Characterization of the Protein Component of the GMP-140 Ligand on Neutrophils

Figure 5:
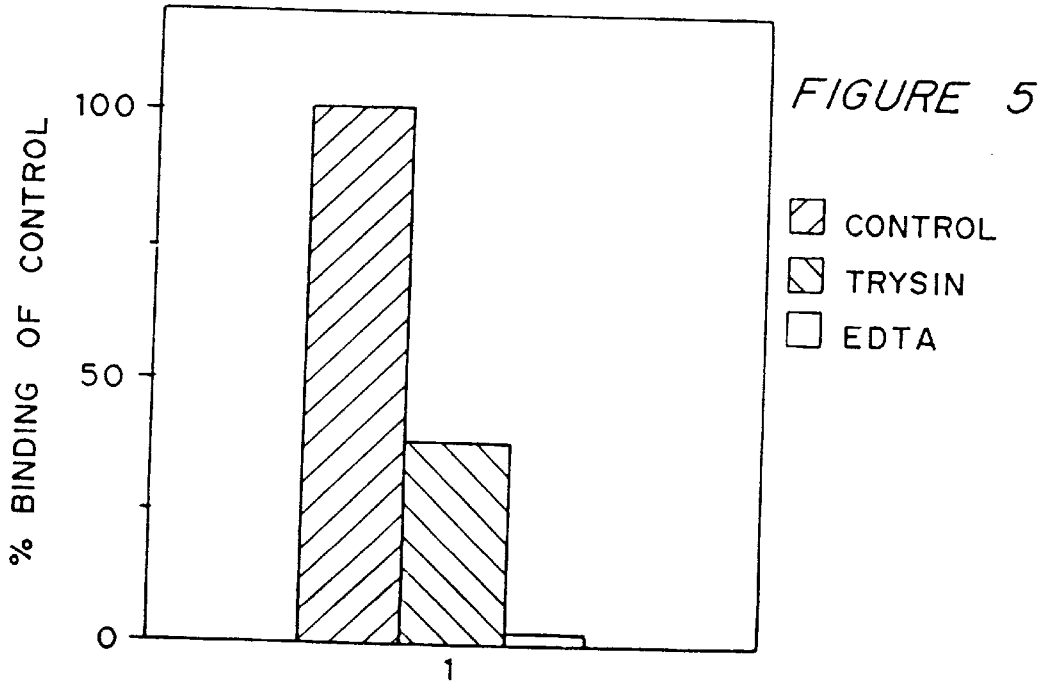
FIG. 5 is a graph of the effect of trypsin on binding of Neo Lewis CHO cells to immobilized GMP-140, % binding of control for control (dark bar), treated with trypsin (///), and in the presence of EDTA (light bar).

Treatment of neutrophils with trypsin abolished specific GMP-140 binding, indicating that the predominant ligand for GMP-140 on neutrophils is surface glycoprotein rather than glycospingolipid. Trypsin treatment of NeoLewis CHO cells also significantly reduced their adhesion to GMP-140, as shown in FIG. 5, indicating that glycoprotein components are also major ligands for GMP-140 on these cells. A glycolipid ligand would not be expected on the NeoLewis CHO cells, since the simple glycolipids synthesized by CHO cells would not be substrates for the transfected fucosyltransferase. The surface proteins bearing the oligosacharide structures recognized by GMP-140 are unlikely to be the same in human myeloid cells and chinese hamster ovary cells. This suggests that high affinity binding of GMP-140 to its ligand does not require a protein-protein interaction.

For trypsin treatment, NeoLewis CHO cells suspended in HEPES buffer A were incubated for 10 min at 37° C. with 0.1% DPCC-trypsin. Control cells were incubated under identical conditions with DPCC-trypsin that had been irreversibly inactivated with DFP. After trypsin treatment, cells were chilled on ice and DFP added to 2 mM final concentration to inactivate the enzyme. After treatment with trypsin the cells were washed twice with ice-cold HEPES buffer A prior to assay.

In the case of neutrophils, it has been established that a major glycoprotein recognized by GMP-140,has an apparent Mr of approximately 120,000 as analyzed by SDS-PAGE under reducing conditions. A plasma membrane fraction of human neutrophils was prepared and the material analyzed by “ligand blotting.” The material was fractionated by SDS-PAGE, transferred to Immobilon membranes, and probed with [$^{125}$]GMP-140. Consistent binding of labeled GMP-140 to a 120-kD band under reducing conditions was observed. The binding is specific, because it is $Ca^{2+}$-dependent, blocked by antibody G1 but not S12, and eliminated by prior treatment of the membrane with neuraminidase. This protein is bound quantitatively on a wheat germ agglutinin affinity column, indicating that it contains extensively sialylated oligosaccharides.

The protein binds to and can be eluted from an affinity column of GMP-140 coupled to Affigel. The partially purified protein stains poorly with silver and Coomassie blue. The protein may represent a heavily O-glycosylated protein known as leukosialin, which has a similar apparent Mr and staining pattern on SDS polyacrylamide gels. In addition, treatment of the protein with low doses of neuraminidase, which does not remove all the sialic acid from the protein, results in slower mobility on gels, a pattern consistent with partial desiaylation of certain heavily O-glycosylated proteins.

There may be other proteins on myeloid cells which carry the oligosaccharide ligand for GMP-140. As determined by ligand blotting, the 120-kDa glycoprotein may represent the most abundant ligand and/or the structure that binds with greatest affinity to GMP-140.

Preparation of Diagnostic and Therapeutic Agents from Carbohydrates Interacting with GMP-140

The carbohydrates described above have a variety of applications as diagnostic reagents and, potentially, in the treatment of numerous inflammatory disorders.

Diagnostic Reagents

Antibodies or other probes to the carbohydrate can be used for the detection of human disorders in which GMP-140 ligands might be defective. Such disorders would most likely be seen in patients with increased susceptibility to infections in which leukocytes might not be able to bind to activated platelets or endothelium. Cells to be tested, usually leukocytes, are collected by standard medically approved techniques and screened. Detection systems include. ELISA procedures, binding of radiolabeled antibody to immobilized activated cells, flow cytometry, or other methods known to those skilled in the arts. Leukocytes deficient in ligands for GMP-140 would demonstrate defective binding of antibodies to the ligand or of GMP-140 itself.

A similar approach can be used to determine qualitative or quantitative disorders of GMP-140. The carbohydrate is labeled radioactively, with a fluorescent tag, enzymatically, or with electron dense material such as gold for electron microscopy. The labeled carbohydrates, or appropriate derivatives thereof, are tested for their ability to bind to GMP-140 on activated platelets from patients with disorders in which GMP-140 might be defective.

Clinical Applications

Since GMP-140 has several functions related to leukocyte adherence, inflammation, and coagulation, clinically, compounds which interfere with binding of GMP-140 and/or the other selecting, including ELAM-1 and LEU-8, such as the carbohydrates, can be used to modulate these responses.

For example, the carbohydrates can be used to competitively inhibit leukocyte adherence by competitively binding to GMP-140 on the surface of activated platelets or endothelial cells. This kind of therapy would be particularly useful in acute situations where effective, but transient, inhibition of leukocyte-mediated inflammation is desirable. Chronic therapy by infusion of carbohydrate may also be feasible in some circumstances.

An inflammatory response may cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67: 1016–1023, 1983). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces,. including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is not known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, suggesting a role for platelets in the spread of some cancers.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis.

In these clinical applications, the carbohydrate, or mixture of carbohydrate, in an appropriate pharmaceutical carrier, is preferably administered intravenously where immediate relief is required. The carbohydrate(s) can also be administered intramuscularly, intraperitoneally, subcutaneously, orally, as the carbohydrate, conjugated to a carrier molecule, or in a drug delivery device. The carbohydrate can additionally be modified chemically to increase its in vivo half-life.

The carbohydrate can be isolated from cells expressing the carbohydrate, either naturally or as a result of genetic engineering as described in the transfected COS cell examples, or, preferably, by synthetic means. These methods are known to those skilled in the art. In addition, a large number of glycosyltransferases have been cloned (J. C. Paulson and K. J. Colley, *J. Biol. Chem.* 264: 17615–17618, 1989). Accordingly, workers skilled in the art can use a combination of synthetic chemistry and enzymatic synthesis to make pharmaceuticals or diagnostic reagents.

Carbohydrates that are biologically active are those which inhibit binding of neutrophils and monocytes to GMP-140. Suitable pharmaceutical vehicles for administration to a patient are known to those skilled in the art. For parenteral administration, the carbohydrate will usually be dissolved or suspended in sterile water or saline. For enteral administration, the carbohydrate will be incorporated into an inert carrier in tablet, liquid, or capsular form. Suitable carriers may be starches or sugars and include lubricants, flavorings, binders, and other materials of the same nature. The carbohydrate can also be administered locally at a wound or inflammatory site by topical application of a solution or cream.

Alternatively, the carbohydrate may be administered in, on or as part of, liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the carbohydrate can be incorporated and the microspheres, or composite of microsphetes, implanted for slow release over a period of time, ranging from days to months. See, for example, U.S. Pat. Nos. 4,906,474, 4,925,673, and 3,625,214.

The carbohydrates should be active when administered parenterally or by other means. The amounts needed will be based on concentrations required for inhibition of GMP-140 binding to myeloid cells in in vitro assays and on the clearance rates of the infused carbohydrates. This dosage will be dependent, in part, on whether one or more carbohydrates are administered. A synergistic effect may be seen with combinations of carbohydrates, or with multivalent forms of the natural ligand, or derivatives thereof, designed to increase affinity and/or avidity for GMP-140.

The carbohydrates can also be coated onto substrates for use as prosthetics that are implanted into the body to prevent leukocyte adhesion to platelets or endothelium.

The criteria for assessing response to therapeutic modalities employing antibodies to the carbohydrate is dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response. For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. Neurologic function would be monitored in patients with stroke. Specific tests are used to monitor the functioning of transplanted organs; for example, serum creatinine, urine flow, and serum electrolytes in patients undergoing kidney transplantation.

Modifications and variations of the present invention, methods for modulating binding reactions involving GMP-140 using carbohydrate derived from or forming a portion of the GMP-140 ligand, will be obvious to those skilled in the art from the foregoing detailed description. Such modifications and variations are intended to come within the scope of the appended claims.

I claim:

1. A glycoprotein for binding to GMP-140, the glycoprotein comprising:

an O-linked, fucosylated, sialylated lactosaminoglycan oligosaccharide;

a molecular weight of about 120,000 Daltons as ascertained by SDS-PAGE under reducing conditions; and having affinity binding specific to GMP-140.

2. The glycoprotein of claim 1 wherein the glycoprotein is isolated from neutrophil membranes.

3. The glycoprotein of claim 1 wherein the fucosylated, sialylated lactosaminoglycan oligosaccharide comprises a sialylated Lewis$^x$ group.

4. The glycoprotein of claim 1 wherein the fucosylated, sialylated lactosaminoglycan oligosaccharide comprises an $\alpha$1,3-fucosylated, $\alpha$2,3-sialylated lactosaminoglycan.

5. The glycoprotein of claim 1 wherein the affinity binding specific to GMP-140 is further defined as $Ca^{2+}$-dependent.

6. A glycoprotein for binding to GMP-140, the glycoprotein comprising:

an O-linked, fucosylated, sialylated lactosaminoglycan oligosaccharide; and having affinity binding specific to GMP-140.

7. The glycoprotein of claim 6 wherein the fucosylated, sialylated lactosaminoglycan oligosaccharide comprises a sialylated Lewis$^x$ group.

8. The glycoprotein of claim 6 wherein the fucosylated, sialylated lactosaminoglycan oligosaccharide comprises an $\alpha$1,3-fucosylated, $\alpha$2,3-sialylated lactosaminoglycan.

9. The glycoprotein of claim 6 wherein the affinity binding specific to GMP-140 is further defined as $Ca^{2+}$-dependent.

10. A glycoprotein comprising:

an oligosaccharide portion comprising a sialylated, fucosylated lactosaminoglycan, the oligosaccharide portion O-linked to the glycoprotein;

a molecular weight of about 120,000 Daltons as ascertained by SDS-PAGE under reducing conditions; and wherein the glycoprotein has affinity binding specific to GMP-140.

11. The glycoprotein of claim 10 wherein the glycoprotein is isolated from neutrophil membranes.

12. The glycoprotein of claim 10 wherein the affinity binding specific to GMP-140 is further defined as $Ca^{2+}$-dependent.

13. The glycoprotein of claim 10 wherein the oligosaccharide portion comprises a sialyl Lewis$^x$ group.

14. The glycoprotein of claim 10 wherein the sialylated, fucosylated lactosaminoglycan comprises an $\alpha$1,3 fucosylated, $\alpha$2,3 sialylated lactosaminoglycan.

15. A glycoprotein comprising:

an oligosaccharide portion comprising a sialylated, fucosylated lactosaminoglycan, the oligosaccharide portion O-linked to the glycoprotein; and wherein the glycoprotein has affinity binding specific to GMP-140.

16. The glycoprotein of claim 15 wherein the affinity binding specific to GMP-140 is further defined as $Ca^{2+}$-dependent.

17. The glycoprotein of claim 15 wherein the oligosaccharide portion comprises a sialyl Lewis$^x$ group.

18. The glycoprotein of claim 15 wherein the sialylated, fucosylated lactosaminoglycan comprises an $\alpha$1,3 fucosylated, $\alpha$2,3 sialylated lactosaminoglycan.

* * * * *

UNITED STATES PATENT AND TRADEMARK OFFICE
CERTIFICATE OF CORRECTION

PATENT NO. : 5,929,036
DATED : July 27, 1999
INVENTOR(S) : Rodger P. McEver

It is certified that error appears in the above-identified patent and that said Letters Patent is hereby corrected as shown below:

Title page, Item [54] and Column 1, line 1,
Title, delete "OR" and substitute therefor -- FOR --.

Title page,
Item [57], ABSTRACT,
Lines 1 and 9, delete "sialyated" and substitute therefor -- sialylated --

Figure 1B:
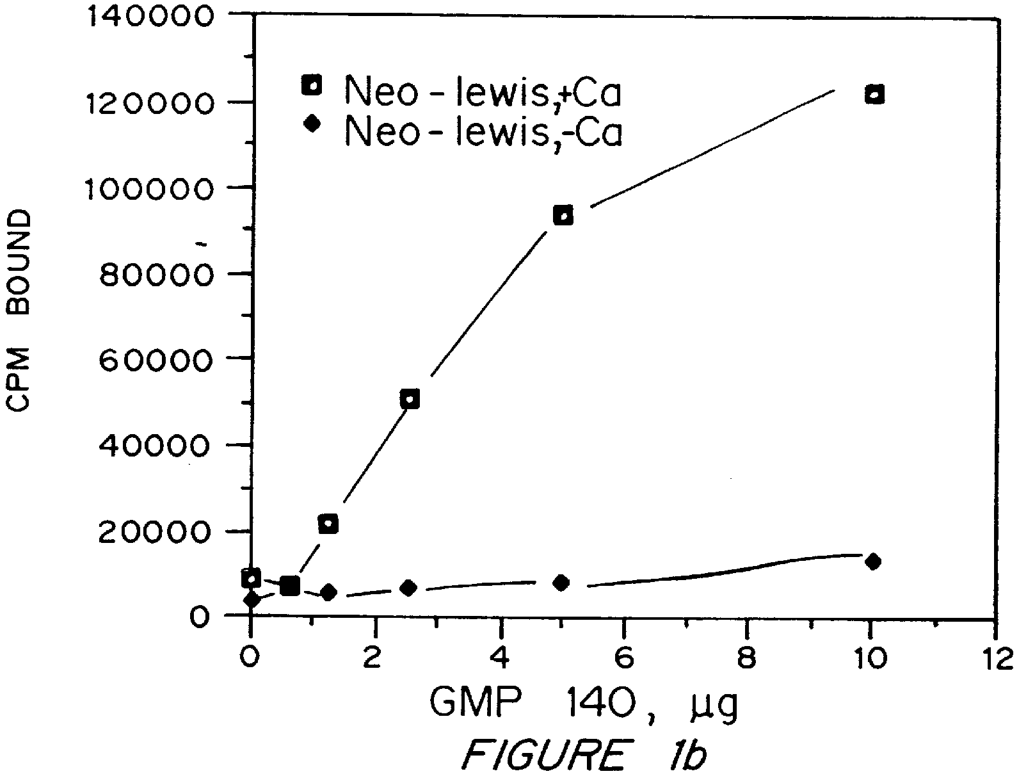
Figure 1C:
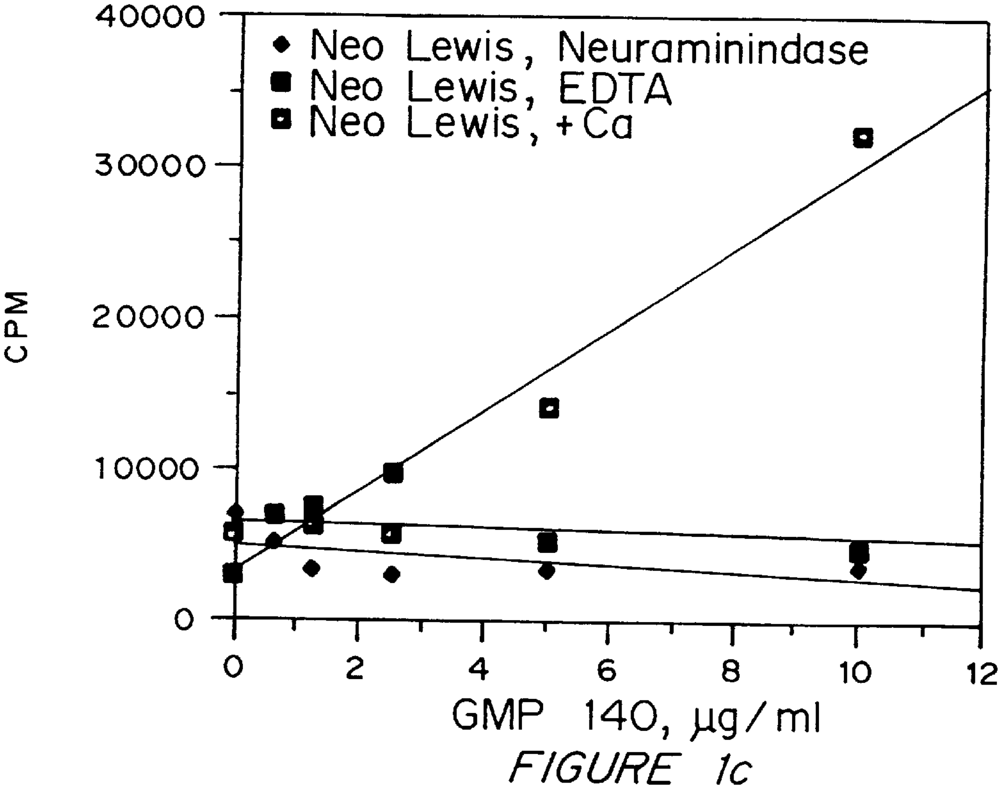
Figure 1D:
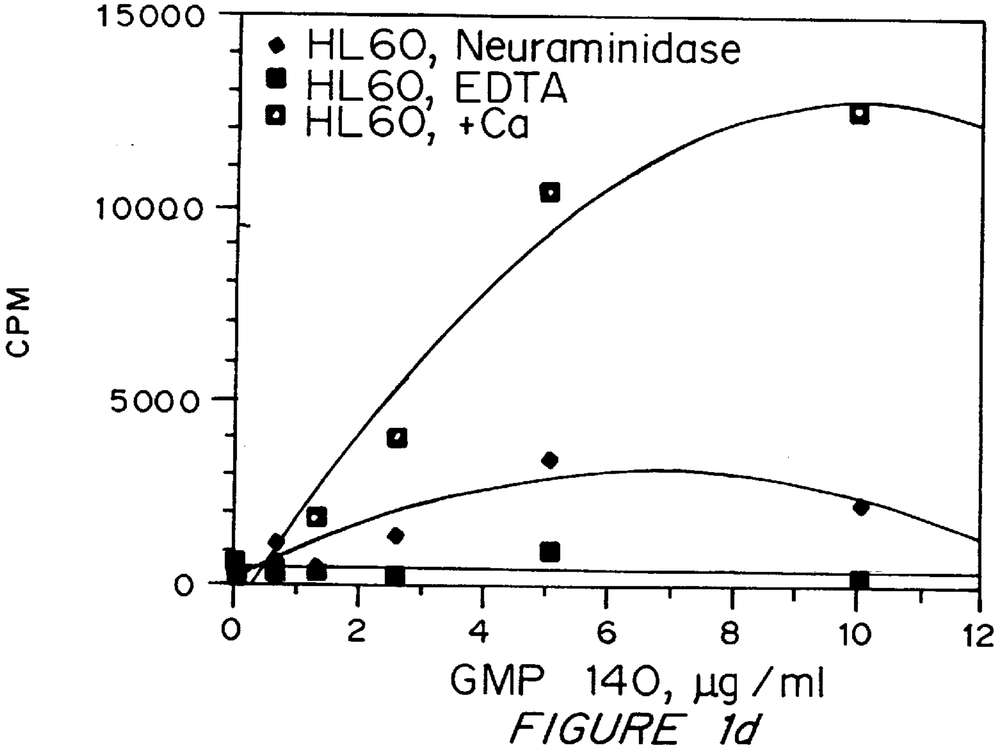

Drawings,
Delete "FIGURE 1a", "FIGURE 1b", "FIGURE 1c" and "FIGURE 1d" and substitute therefor -- FIGURE 1A --, -- FIGURE 1B --, -- FIGURE 1C -- and -- FIGURE 1D --, therefor, respectively.

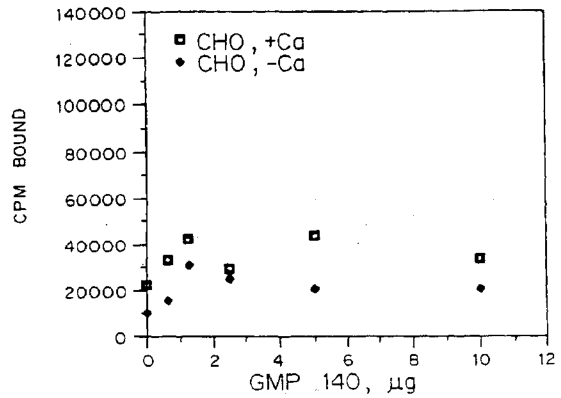

FIGURE 1A

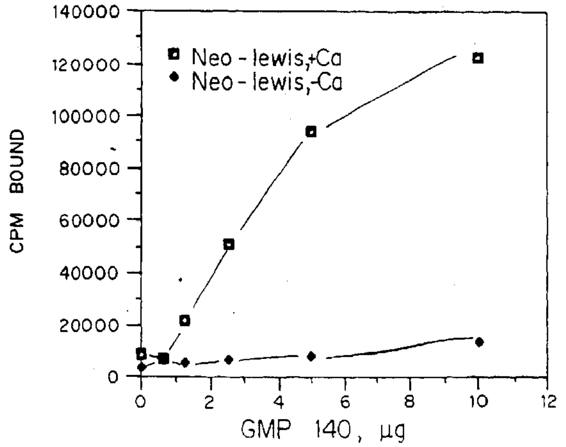

FIGURE 1B

UNITED STATES PATENT AND TRADEMARK OFFICE

CERTIFICATE OF CORRECTION

PATENT NO. : 5,929,036
DATED : July 27, 1999
INVENTOR(S) : Rodger P. McEver

It is certified that error appears in the above-identified patent and that said Letters Patent is hereby corrected as shown below:

<u>Drawings (cont'd),</u>

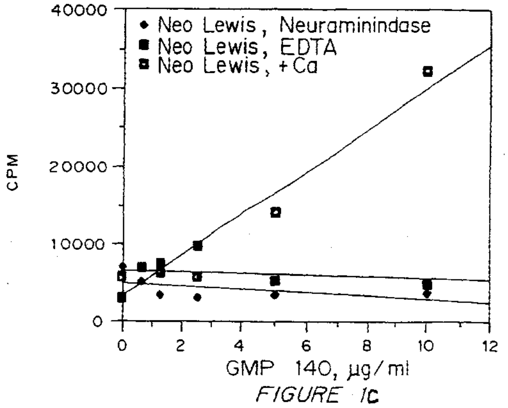

*FIGURE 1C*

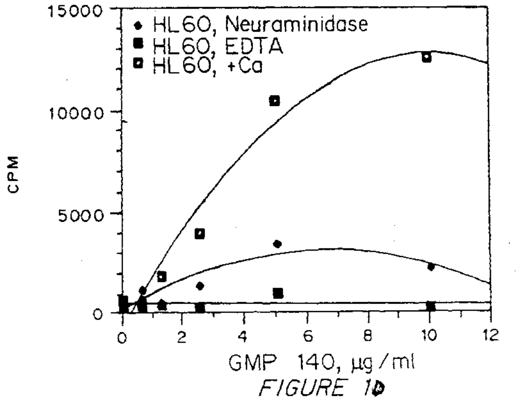

*FIGURE 1D*

Figure 5, delete "TRYSIN" and substitute therefor -- TRYPSIN --

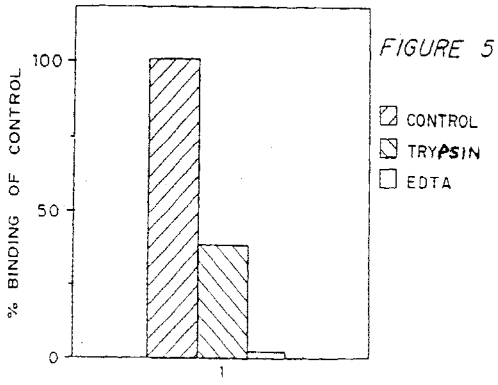

*FIGURE 5*

UNITED STATES PATENT AND TRADEMARK OFFICE
CERTIFICATE OF CORRECTION

PATENT NO. : 5,929,036
DATED : July 27, 1999
INVENTOR(S) : Rodger P. McEver

It is certified that error appears in the above-identified patent and that said Letters Patent is hereby corrected as shown below:

Column 2,
Line 28, delete "selecting"," and substitute -- "selectins" --, therefor.
Line 61, delete "selecting," and substitute -- selectins, -- therefor.

Column 3,
Line 61, delete "selecting" and substitute therefor -- selectins --.

Column 4,
Lines 5 and 13, delete "sialyated" and substitute -- sialylated -- therefor.
Line 40, delete "coated" and substitute -- coat -- therefor.
Line 54, delete "(dark bar)," and substitute therefor -- (/ /) --.
Line 55, delete "(///)," and substitute therefor -- (\\\), --.
Line 56, delete "(++++)," and substitute therefor -- (\ \ \), --.
Line 56, delete "(/ / /)." and substitute therefor -- (blank). --.

Column 5,
Line 10, delete "(dark bar)," and substitute therefor -- (///), --.
Line 10, delete "(///)." and substitute therefor -- (\\\). --.
Lines 14, 22 and 45, delete "sialyated" and substitute -- sialylated -- therefor.

Column 6,
Line 7, delete "sialyated" and substitute -- sialylated -- therefor.
Line 45, delete "concentrtions" and substitute -- concentrations -- therefor.

Column 8,
Lines 21-22, delete "polylactosmainoglycans" and substitute therefor -- polylactosaminoglycans --.
Line 31, delete "Sialyated" and substitute -- Sialylated -- therefor.
Table 1, right-hand column ("CELL TYPE"), lines 1 and 4, delete "NeoLewis," and substitute therefor -- NeoLew, --.

UNITED STATES PATENT AND TRADEMARK OFFICE

CERTIFICATE OF CORRECTION

PATENT NO. : 5,929,036
DATED : July 27, 1999
INVENTOR(S) : Rodger P. McEver

It is certified that error appears in the above-identified patent and that said Letters Patent is hereby corrected as shown below:

Columns 9 and 10,
Table 1, Reformat as follows:

TABLE I - continued

OLIGOSACCHARIDE STRUCTURE OF CELL TYPES

| OLIGOSACCHARIDE STRUCTURE | COMMON DESIGNATION | CELL TYPE |
|---|---|---|
| Fucα1-3<br>Galβ1-4GlcNAcβ1-3Galβ1-4GlcNAcβ1-3Galβ1-4GlcNAcβ1 | SSEA-1 | NeoLew, NeoLew(Rel) |
| Fucα1-3<br>NeuAcα2-3 Galβ1-4GlcNAcβ1-3Galβ1-4GlcNAcβ1-3Galβ1-4GlcNAcβ1 | S-Le$^x$ | NeoLew |
| Fucα1-3<br>NeuAcα2-3 Galβ1-4GlcNAcβ1-3Galβ1-4GlcNAcβ1-3Galβ1-4GlcNAcβ1 | VIM-2 | NeoLew, NeoLew(Rel) |
| Fucα1-3 Fucα1-3<br>NeuAcα2-3 Galβ1-4GlcNAcβ1-3Galβ1-4GlcNAcβ1-3Galβ1-4GlcNAcβ1 | difucosyl-S-Le$^x$ | NeoLew |

Column 12,
Line 14, delete "$Ca^{+2}$ and $Mg^{+2}$," and substitute therefor -- $Ca^{2+}$ and $Mg^{2+}$ --.
Line 16, delete "HG-DNEK/10%" and substitute therefor -- HG-DNEM/10% -- therefor.
Line 38, delete "Nature" and substitute therefor -- *Nature* --.

Column 13,
Line 28, delete "oligosacharide" and substitute -- oligosaccharide -- therefor.

Column 14,
Line 42, delete "selecting," and substitute therefor -- selectins, --.

Column 16,
Line 47, delete "microsphetes," and substitute -- microspheres, -- therefor.

Signed and Sealed this

Seventeenth Day of August, 2004

JON W. DUDAS
*Acting Director of the United States Patent and Trademark Office*